United States Patent
Basu et al.

(10) Patent No.: US 10,987,045 B2
(45) Date of Patent: Apr. 27, 2021

(54) BASKET CATHETER WITH INDIVIDUAL SPINE CONTROL

(71) Applicant: Biosense Webster (Israel) Ltd., Yokneam (IL)

(72) Inventors: Shubhayu Basu, Anaheim, CA (US); Mario A. Solis, Rancho Cucamonga, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 229 days.

(21) Appl. No.: 14/853,668

(22) Filed: Sep. 14, 2015

(65) Prior Publication Data

US 2017/0071544 A1    Mar. 16, 2017

(51) Int. Cl.
    *A61B 5/042*    (2006.01)
    *A61B 5/287*    (2021.01)
    *A61B 5/00*    (2006.01)
    *A61B 5/333*    (2021.01)

(52) U.S. Cl.
    CPC .............. *A61B 5/287* (2021.01); *A61B 5/333* (2021.01); *A61B 5/6858* (2013.01); *A61B 5/6859* (2013.01); *A61B 2562/227* (2013.01); *A61M 2205/0266* (2013.01)

(58) Field of Classification Search
    CPC ................ A61B 5/0422; A61B 5/6858; A61B 2018/00267
    See application file for complete search history.

(56) References Cited

U.S. PATENT DOCUMENTS

| | | | |
|---|---|---|---|
| 4,699,147 | A | 10/1987 | Chilson et al. |
| 5,237,996 | A * | 8/1993 | Waldman ............ A61B 5/0422 |
| | | | 600/374 |
| 5,239,724 | A | 8/1993 | Salecker et al. |
| 5,255,679 | A | 10/1993 | Imran |
| 5,332,089 | A | 7/1994 | Tillett et al. |
| 5,391,199 | A | 2/1995 | Ben-Haim |
| 5,484,118 | A | 1/1996 | Fujimura et al. |
| 5,618,612 | A | 4/1997 | Gstrein |
| 5,690,963 | A | 11/1997 | Spargo et al. |
| 5,772,590 | A | 6/1998 | Webster, Jr. |

(Continued)

FOREIGN PATENT DOCUMENTS

| | | |
|---|---|---|
| JP | H 08-504333 | 6/1995 |
| JP | H 08-504335 A | 6/1995 |

(Continued)

OTHER PUBLICATIONS

European Search Report in corresponding European Patent Application No. 16188474.7, completed Feb. 1, 2017, pp. 1-8.

(Continued)

*Primary Examiner* — Eun Hwa Kim

(74) *Attorney, Agent, or Firm* — Dergosits & Noah LLP; Todd A. Noah

(57) ABSTRACT

This disclosure is directed to a catheter having a basket-shaped electrode assembly formed from a plurality of spines, each with a plurality of electrodes. The spines are connected at their distal ends and extend through the catheter body to its proximal end. Each spine may be independently controlled, such as by adjusting its longitudinal position relative to the catheter body to causes it to bow outwards to a greater or lesser degree.

14 Claims, 6 Drawing Sheets

(56) References Cited

U.S. PATENT DOCUMENTS

| | | | |
|---|---|---|---|
| 5,908,446 A | 6/1999 | Imran | |
| 5,935,440 A | 8/1999 | Bratton et al. | |
| 5,938,694 A * | 8/1999 | Jaraczewski | A61B 5/0422 607/122 |
| 6,052,607 A * | 4/2000 | Edwards | A61B 5/6859 600/374 |
| 6,064,905 A | 5/2000 | Webster et al. | |
| 6,174,318 B1 | 1/2001 | Bates et al. | |
| 6,239,724 B1 | 5/2001 | Doron et al. | |
| 6,332,089 B1 | 12/2001 | Acker et al. | |
| 6,484,118 B1 | 11/2002 | Govari | |
| 6,544,262 B2 * | 4/2003 | Fleischman | A61B 18/1492 600/374 |
| 6,618,612 B1 | 9/2003 | Acker et al. | |
| 6,690,963 B2 | 2/2004 | Ben-Haim et al. | |
| 6,748,255 B2 | 6/2004 | Fuimaono et al. | |
| 6,973,340 B2 | 12/2005 | Fuimaono et al. | |
| 7,377,906 B2 | 5/2008 | Selkee | |
| 8,137,308 B2 | 3/2012 | Schultz | |
| 8,825,130 B2 * | 9/2014 | Just | A61B 18/1492 600/374 |
| 8,945,116 B2 | 2/2015 | MacAdam et al. | |
| 10,602,947 B2 | 3/2020 | Govari et al. | |
| 2002/0065455 A1 | 5/2002 | Ben-Haim et al. | |
| 2003/0120150 A1 | 6/2003 | Govari | |
| 2004/0068178 A1 | 4/2004 | Govari | |
| 2005/0119647 A1 | 6/2005 | He et al. | |
| 2012/0209262 A1 | 8/2012 | Falwell et al. | |
| 2014/0305699 A1 | 10/2014 | Govari | |
| 2014/0309512 A1 | 10/2014 | Govari | |

FOREIGN PATENT DOCUMENTS

| | | |
|---|---|---|
| JP | H 08-510677 A | 9/1995 |
| JP | 2002-126096 A | 5/2002 |
| JP | 2007-537832 A | 12/2007 |
| JP | 2014-204986 A | 10/2014 |
| WO | 1994/007412 | 4/1994 |
| WO | 1994/012098 | 6/1994 |
| WO | 199601557 | 1/1996 |
| WO | 1996002100 | 1/1996 |
| WO | 96/05768 | 2/1996 |
| WO | WO97/17892 * | 5/1997 |
| WO | 2005/115226 A2 | 12/2005 |

OTHER PUBLICATIONS

U.S. Appl. No. 13/860,921.
U.S. Appl. No. 14/063,477.
Search Report from Japanese Patent Application No. 2016-178298, dated Jun. 30, 2020.

* cited by examiner

BASKET CATHETER WITH INDIVIDUAL SPINE CONTROL

FIELD OF THE PRESENT DISCLOSURE

This invention relates to electrophysiologic (EP) catheters, in particular, EP catheters for mapping and/or ablation in the heart.

BACKGROUND

Electrophysiology catheters are commonly-used for mapping electrical activity in the heart. Various electrode designs are known for different purposes. For example, catheters having basket-shaped electrode arrays are known and described, for example, in U.S. Pat. Nos. 5,772,590, 6,748, 255 and 6,973,340, the entire disclosures of each of which are incorporated herein by reference.

Basket catheters typically have an elongated catheter body and a basket-shaped electrode assembly mounted at the distal end of the catheter body. The basket assembly has proximal and distal ends and comprises a plurality of spines connected at their proximal and distal ends. Each spine comprises at least one electrode. The basket assembly has an expanded configuration wherein the spines bow radially outwardly and a collapsed configuration wherein the spines are arranged generally along the axis of the catheter body.

It is desirable that a basket assembly be capable of detecting in as few beats as possible, including a single beat, as much of the electrical function of the region in which the electrode assembly is deployed, such as the left or right atrium. Conventional basket-shaped electrode assemblies are generally spherical or otherwise describe a smoothly rounded compact volume in which the spines, and correspondingly the electrodes, are constrained to the outer surface of the shape. However, the heart chamber or other region in which the catheter is deployed may not match the shape of the basket-shaped electrode assembly, resulting in a suboptimal degree of contact between one or more of the electrodes carried by the spines and the tissue being investigated.

Accordingly, it would be desirable to provide an EP mapping catheter that offers increased contact with an irregularly shaped heart chamber or other body cavity. As such, it would be desirable to provide such a catheter with spines that may be controlled individually to allow them to more readily conform to surrounding walls of tissue. The techniques of this disclosure as described in the following materials satisfy these and other needs.

SUMMARY

The present disclosure is directed to a catheter with an elongated catheter body having proximal and distal ends and at least one lumen therethrough and a basket-shaped electrode assembly at the distal end of the catheter body, the basket-shaped electrode assembly formed by a plurality of spines connected at their distal ends, each spine having a plurality of electrodes and extending through the lumen of the catheter body to the proximal end, wherein each spine is independently controlled.

In one aspect, each spine may be independently controlled by adjusting a longitudinal position relative to the catheter body.

In one aspect, the basket-shaped electrode assembly may have an expanded configuration in which the spines bow radially outwardly when unconstrained and a collapsed configuration in which the spines are arranged generally along a longitudinal axis of the catheter body. Each spine may be in a retracted position within respect to the catheter body when in the collapsed configuration. Each of the spines may bow outwards to a greater degree when the spine is positioned relatively more distally to increase an unconstrained length when the basket-shaped electrode assembly is in the expanded configuration. Further, each of the spines may bow outwards to a lesser degree when the spine is positioned relatively more proximally to decrease an unconstrained length when the basket-shaped electrode assembly is in the expanded configuration.

In one aspect, each spine may have an actuator at a proximal end. Each actuator may include a connector for coupling leads to the electrodes on the spine.

In one aspect, each spine may be formed from a shape memory material.

This disclosure also provides a method for mapping a cavity of the body. An elongated catheter body may be provided, the catheter body having proximal and distal ends and at least one lumen therethrough and a basket-shaped electrode assembly at the distal end of the catheter body, the basket-shaped electrode assembly comprising a plurality of spines connected at their distal ends, each spine comprising a plurality of electrodes and extending through the lumen of the catheter body to the proximal end, the distal end of the catheter may be introduced into the cavity, the basket-shaped electrode assembly may be expanded from a collapsed configuration wherein the spines are arranged generally along a longitudinal axis of the catheter body to an expanded configuration, at least one of the spines may be independently controlled to increase contact between at least a portion of the electrodes of the spine with tissue forming the cavity and electrical data received from the at least a portion of the electrodes in contact with the tissue may be recorded.

In one aspect, independently controlling at least one of the spines may include adjusting a longitudinal position of the at least one spine relative to the catheter body.

In one aspect, the spines may bow radially outwardly when in the expanded configuration. As such, independently controlling at least one of the spines may include positioning the at least one spine relatively more distally to cause the at least one spine to increase an unconstrained length and bow outwards to a greater degree. Alternatively or in addition, independently controlling at least one spine may include positioning the at least one spine relatively more proximally to decrease an unconstrained length and cause the at least one spine to bow outwards to a lesser degree.

In one aspect, the cavity of the body may be an atrium of the heart.

In one aspect, a plurality of the spines may be independently controlled.

BRIEF DESCRIPTION OF THE DRAWINGS

Further features and advantages will become apparent from the following and more particular description of the preferred embodiments of the disclosure, as illustrated in the accompanying drawings, and in which like referenced characters generally refer to the same parts or elements throughout the views, and in which.

DETAILED DESCRIPTION

Figure 1:
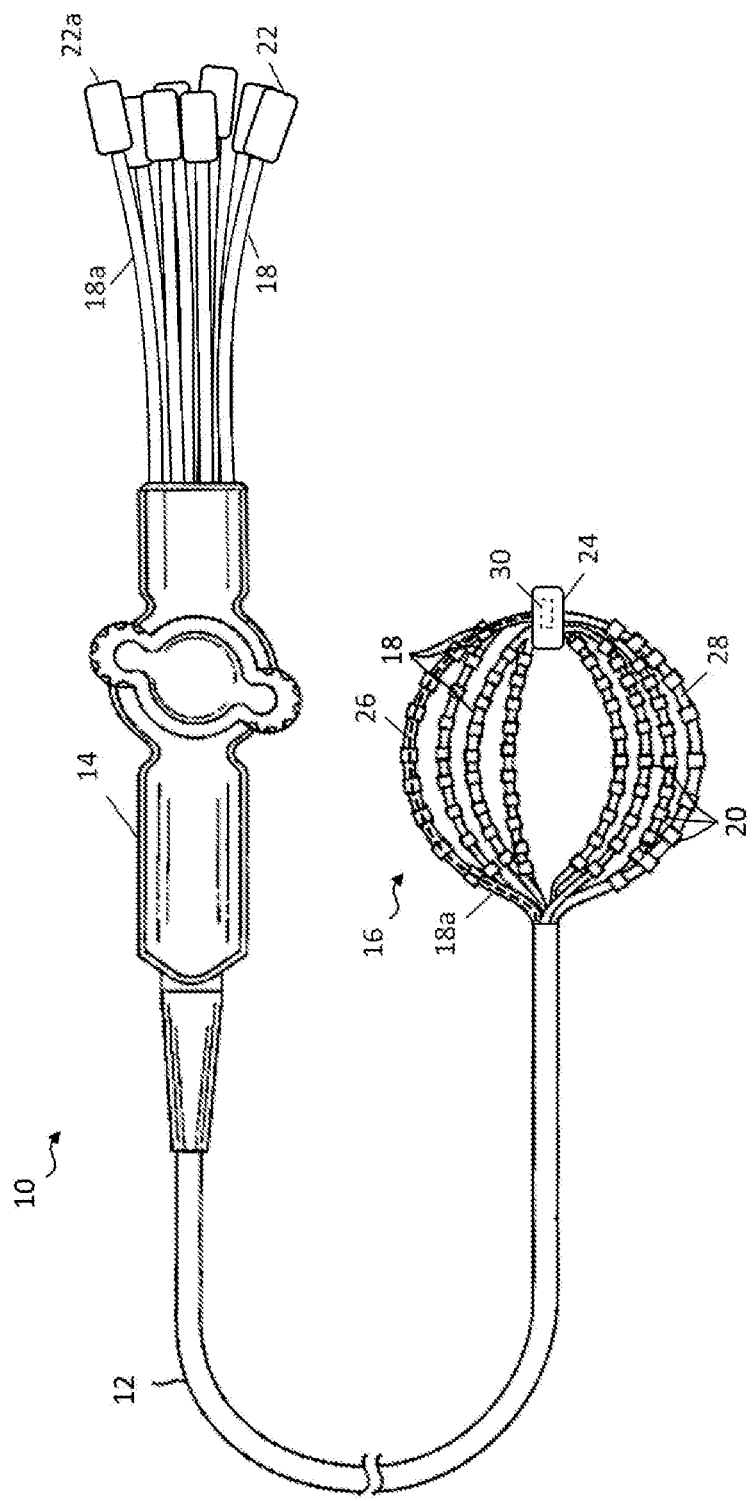
FIG. 1 is a top plan view of a catheter of the present invention, with a basket-shaped electrode assembly with independently controlled spines in an expanded configuration, according to one embodiment.

At the outset, it is to be understood that this disclosure is not limited to particularly exemplified materials, architectures, routines, methods or structures as such may vary. Thus, although a number of such options, similar or equivalent to those described herein, can be used in the practice or embodiments of this disclosure, the preferred materials and methods are described herein.

It is also to be understood that the terminology used herein is for the purpose of describing particular embodiments of this disclosure only and is not intended to be limiting.

The detailed description set forth below in connection with the appended drawings is intended as a description of exemplary embodiments of the present disclosure and is not intended to represent the only exemplary embodiments in which the present disclosure can be practiced. The term "exemplary" used throughout this description means "serving as an example, instance, or illustration," and should not necessarily be construed as preferred or advantageous over other exemplary embodiments. The detailed description includes specific details for the purpose of providing a thorough understanding of the exemplary embodiments of the specification. It will be apparent to those skilled in the art that the exemplary embodiments of the specification may be practiced without these specific details. In some instances, well known structures and devices are shown in block diagram form in order to avoid obscuring the novelty of the exemplary embodiments presented herein.

For purposes of convenience and clarity only, directional terms, such as top, bottom, left, right, up, down, over, above, below, beneath, rear, back, and front, may be used with respect to the accompanying drawings. These and similar directional terms should not be construed to limit the scope of the disclosure in any manner.

Unless defined otherwise, all technical and scientific terms used herein have the same meaning as commonly understood by one having ordinary skill in the art to which the disclosure pertains.

Finally, as used in this specification and the appended claims, the singular forms "a, "an" and "the" include plural referents unless the content clearly dictates otherwise.

Certain types of electrical activity within a heart chamber are not cyclical. Examples include arterial flutter or arterial fibrillation, and ventricular tachycardia originating in scars in the wall of the ventricle that have resulted from infarcts. Such electrical activity is random from beat to beat. To analyze or 'map' this type of electrical activity, it is desirable to obtain the 'picture' as quickly as possible, such as within one heartbeat. In other words, all the points of the map or picture may be obtained simultaneously within one-tenth of a second. According to the techniques of this disclosure, a basket catheter with an electrode assembly of individually controlled spines may conform more closely to the anatomy of the patient's heart in order to accurately map this electrical activity.

As shown in FIG. 1, the catheter 10 may include an elongated catheter body 12, with a control handle 14 at its proximal end. A basket-shaped electrode assembly 16 may be located at the distal end of catheter body, and may be formed from a plurality of spines 18, each carrying multiple electrodes 20, mounted at the distal end of the catheter body 12. The catheter body 12 comprises an elongated tubular construction having a single, axial or central lumen (not shown), but can optionally have multiple lumens if desired. To enable accurate mapping of electrical signals, for example to detect most or substantially all of the electrical function of the right or left atrium in as little as a single heartbeat, it may be desirable to provide an array of electrodes. As such, numbers of spines 18 employed may be five to twelve or any other suitable number. Spines 18 may be evenly or unevenly distributed radially. Further, each spine 18 may include multiple electrodes 20, such as approximately five to thirty electrodes per spine, although other numbers can be employed depending on the application. Similarly, the electrodes may be evenly distributed along the spine or may be skewed proximally, centrally or distally to facilitate analysis of the measured electrical signals.

In one aspect, spines 18 may include a material, such as a shape memory material as described below, that facilitates assuming an expanded configuration to bring electrodes 20 into contact or closer proximity with tissue lining the walls of the cavity in which basket-shaped electrode assembly 16 is deployed. Notably, as shown in FIG. 1, in one embodiment spines 18 may have a pre-shaped configuration in which they bow radially outwards from the longitudinal axis of catheter 10. Spines 18 may be sized appropriately depending on the patient's anatomy to provide a close fit to the area of the patient being investigated, such as the right or left atria. At the proximal end of basket-shaped electrode assembly 16, spines 18 are freed from the constraint of being disposed within catheter body 12 and the distal ends of spines 18 may be secured together, such as by distal cap 24. As such, spines 18 may bow outwards from the longitudinal axis of catheter 10 into the expanded configuration.

According to the techniques of this disclosure, each spine 18 may be individually controllable. As shown, spines 18 are routed through catheter body 12 so that they extend to the proximal end of catheter and may terminate in actuators 22 to allow manipulation of each spine 18 to adjust its position longitudinally relative to catheter body 12. When a spine is moved relatively distally in the longitudinal direction, a greater length emerges from catheter body 12 and is freed from constraint. The distal end of basket-shaped electrode assembly 16 is held in relative position by the remaining spines, or any other suitable mechanism such as a central wire. As a result, the spine being advanced longitudinally bows outwards to a greater degree. Correspondingly, retraction of a spine relative to the others decreases the degree of outward bow. Actuators 22 may also provide suitable connections for leads coupled to electrodes 20. Thus, each spine has a corresponding actuator, such as spine 18a and actuator 22a as indicated. Longitudinal movement of each spine 18 with respect to catheter body 12 may be used tailor the degree to which each spine bows outward in order to more closely conform to the surrounding tissue. As such, the degree of contact with which one or more electrodes 20 of a given spine engage the walls of the cavity in which basket-shaped electrode assembly 16 is positioned may be adjusted as desired.

Figure 2:
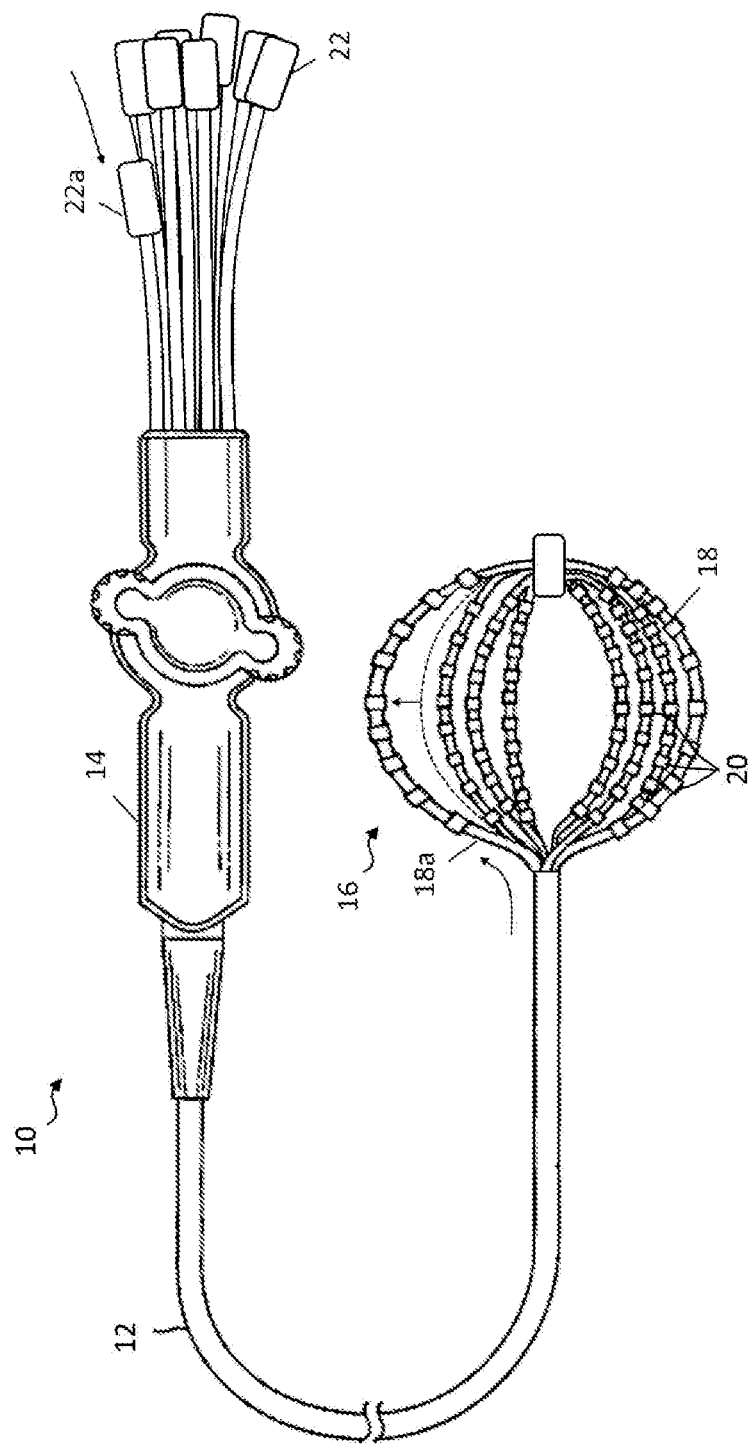
FIG. 2 is a schematic view of the basket-shaped electrode assembly of FIG. 1 in which one spine is positioned relatively more distally, according to one embodiment.

A schematic illustration of this operation is depicted in FIG. 2. In comparison to the configuration shown in FIG. 1, one spine, spine 18a, has been advanced longitudinally relative to catheter body 12, such as by manipulation of actuator 22a. As discussed above, this causes the portion of spine 18a in basket-shaped electrode assembly 16 to deflect further outwards from the longitudinal axis. Although not shown, relative motion of spine 18a in the proximal direction may provide the opposite result and reduce the amount of outward deflection. Correspondingly, the relative position of each spine 18 may be adjusted as desired in order to achieve a greater degree of contact with and/or more closely conform to the tissue forming the surrounding walls.

As depicted in FIG. 1, each spine 18 may comprise a core flexible wire 26 (shown in phantom) with a non-conductive covering 28 on which one or more of the ring electrodes 20 are mounted. In an embodiment, the flexible wires 26 may be formed from a shape memory material to facilitate the transition between expanded and collapsed configurations and the non-conductive coverings 28 may each comprise a biocompatible plastic tubing, such as polyurethane or polyimide tubing. For example, nickel-titanium alloys known as nitinol may be used. At body temperature, nitinol wire is flexible and elastic and, like most metals, nitinol wires deform when subjected to minimal force and return to their shape in the absence of that force. Nitinol belongs to a class of materials called Shaped Memory Alloys (SMA) that have interesting mechanical properties beyond flexibility and elasticity, including shape memory and superelasticity which allow nitinol to have a "memorized shape" that is dependent on its temperature phases. The austenite phase is nitinol's stronger, higher-temperature phase, with a simple cubic crystalline structure. Superelastic behavior occurs in this phase (over a 50°-60° C. temperature spread). Correspondingly, the martensite phase is a relatively weaker, lower-temperature phase with a twinned crystalline structure. When a nitinol material is in the martensite phase, it is relatively easily deformed and will remain deformed. However, when heated above its austenite transition temperature, the nitinol material will return to its pre-deformed shape, producing the "shape memory" effect. The temperature at which nitinol starts to transform to austenite upon heating is referred to as the "As" temperature. The temperature at which nitinol has finished transforming to austenite upon heating is referred to as the "Af" temperature. Accordingly, basket-shaped electrode assembly 16 may have a three dimensional shape that can be easily collapsed to be fed into a guiding sheath and then readily returned to its expanded shape memory configuration upon delivery to the desired region of the patient upon removal of the guiding sheath.

Alternatively, in some embodiments the spines 18 can be designed without the internal flexible wire 26 if a sufficiently rigid nonconductive material is used for the non-conductive covering 28 to permit radial expansion of the basket-shaped electrode assembly 16, so long as the spine has an outer surface that is non-conductive over at least a part of its surface for mounting of the ring electrodes 20.

The catheter body 12 is flexible, i.e., bendable, but substantially non-compressible along its length. The catheter body 12 can be of any suitable construction and made of any suitable material. One construction comprises an outer wall made of polyurethane or PEBAX® (polyether block amide). The outer wall comprises an imbedded braided mesh of stainless steel or the like to increase torsional stiffness of the catheter body 12 so that, when the control handle 14 is rotated, the distal end of the catheter body will rotate in a corresponding manner. The outer diameter of the catheter body 12 is not critical, but generally should be as small as possible and may be no more than about 10 french depending on the desired application. Likewise the thickness of the outer wall is not critical, but may be thin enough so that the central lumen can accommodate a puller wire, lead wires, sensor cables and any other wires, cables or tubes. If desired, the inner surface of the outer wall is lined with a stiffening tube (not shown) to provide improved torsional stability. An example of a catheter body construction suitable for use in connection with the present invention is described and depicted in U.S. Pat. No. 6,064,905, the entire disclosure of which is incorporated herein by reference.

Figure 6:
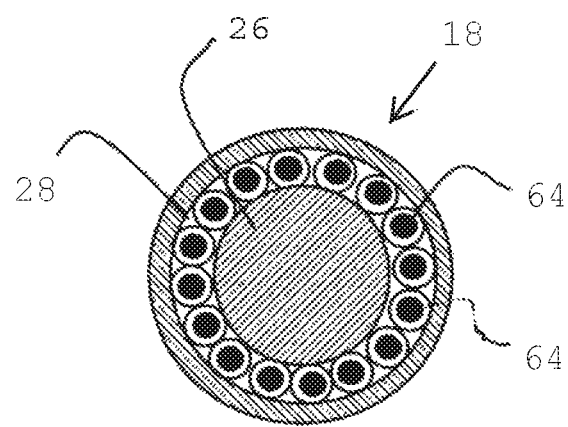
FIG. 6 is a cross-section of an independently controlled spine, according to one embodiment.

In some embodiments, as depicted in FIG. 6, each spine 18 may include a core flexible wire 26 with a non-conductive covering 28 having cabling with built-in or embedded lead wires 64 for the electrodes 20 carried by the spine. Spines 18 having cabling with embedded lead wires is described in U.S. Patent Publication No. 2014/0309512, published Oct. 16, 2014, entitled HIGH DENSITY ELECTRODE STRUCTURE, and U.S. Patent Publication No. 2014/0305699, published Oct. 16, 2014, entitled CONNECTION OF ELECTRODES TO WIRES COILED ON A CORE, the entire disclosures of which are hereby incorporated by reference.

Figure 3:
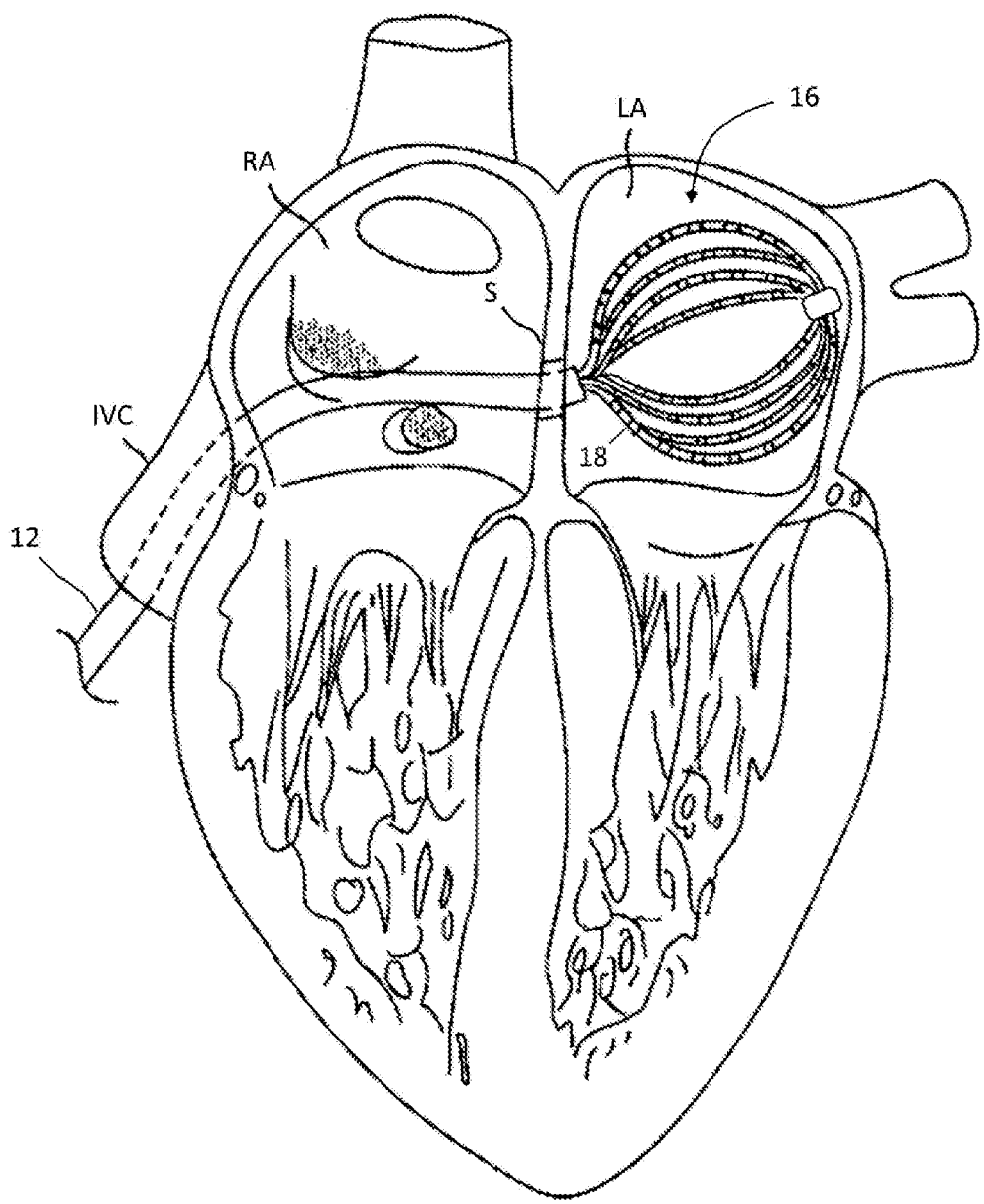
FIG. 3 is a schematic view of a basket-shaped electrode assembly within the left atrium, according to one embodiment.

In one aspect, an electrophysiologist may introduce a guiding sheath, guidewire and dilator into the patient, as is generally known in the art. Examples of suitable guiding sheaths for use in connection with the inventive catheter are the PREFACE™ Braided Guiding Sheath (commercially available from Biosense Webster, Inc., Diamond Bar, Calif.) and the DiRex™ Guiding Sheath (commercially available from BARD, Murray Hill, N.J.). The guidewire is inserted, the dilator is removed, and the catheter is introduced through the guiding sheath whereby the guidewire lumen in the expander permits the catheter to pass over the guidewire. In one exemplary procedure as depicted in FIG. 3, the catheter is first introduced to the right atrium (RA) via the inferior vena cava (IVC), where it passes through the septum (S) in order to reach the left atrium (LA).

As will be appreciated, the guiding sheath covers the spines 18 of the basket-shaped electrode assembly 16 in a collapsed position so that the entire catheter can be passed through the patient's vasculature to the desired location. Once the distal end of the catheter reaches the desired location, e.g., the left atrium as shown, the guiding sheath is withdrawn to expose the basket-shaped electrode assembly 16. Once the guiding sheath is withdrawn, spines 18 flex outwardly to assume their preshaped expanded configuration. As shown in FIG. 3, when each spine 18 is positioned in approximately the same longitudinal position with respect to catheter body 12, basket-shaped electrode assembly 16 has an overall shape similar to conventional basket catheters. However, as can be seen, basket-shaped electrode assembly 16 in this conformation may not conform optimally to the irregularly shaped, non-spherical left atrium. As such, at least some of the electrodes may be far enough away from areas of the tissue to provide accurate measurement of electrical signals.

Figure 4:
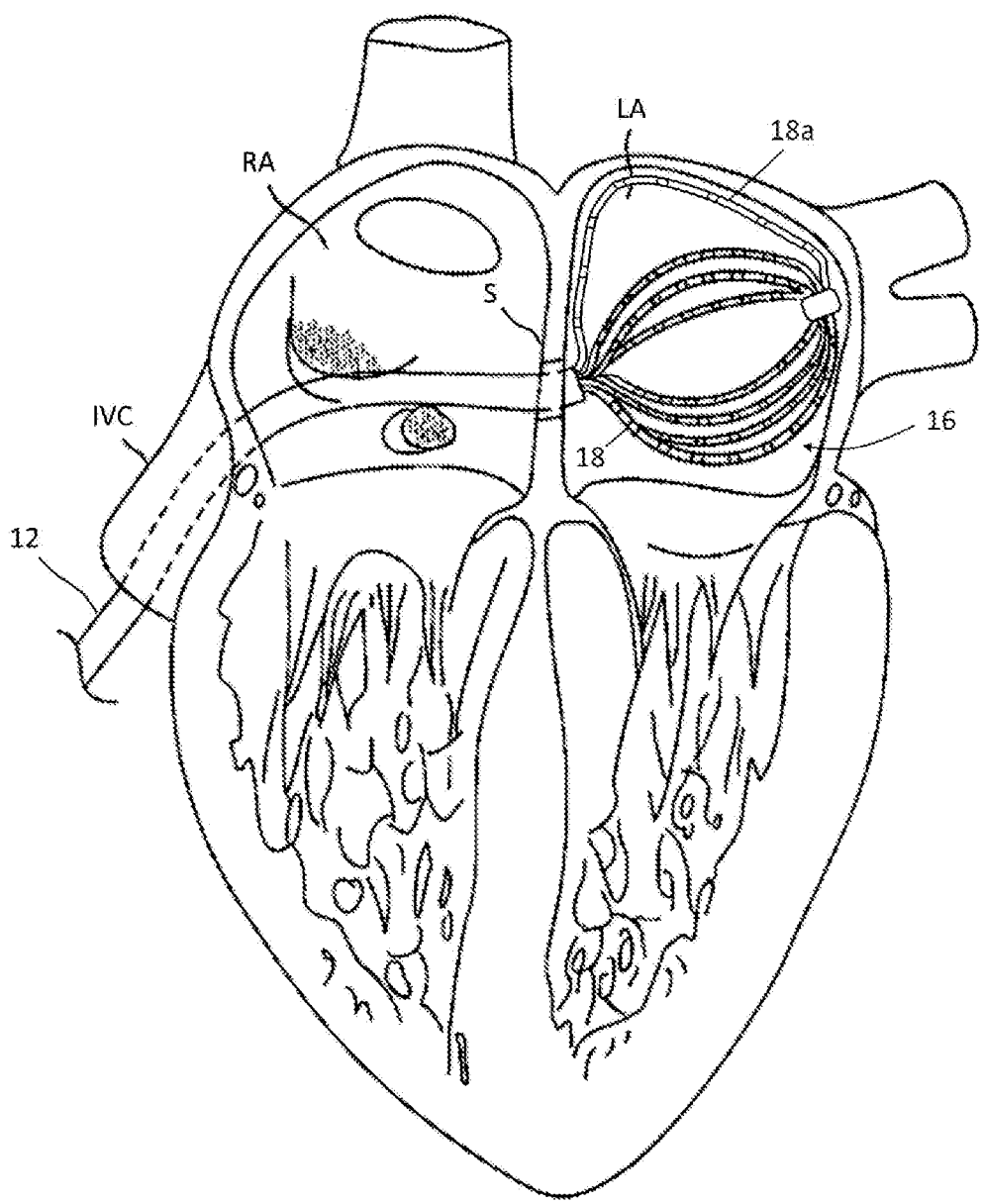
FIG. 4 is a schematic view of the basket-shaped electrode assembly of FIG. 3, in which one spine is positioned relatively more distally to increase contact with atrial tissue, according to one embodiment.

Correspondingly, each spine 18 may be individually controlled as described above to provide improved conformation to the region in which basket-shaped electrode assembly 16 is deployed. As schematically shown in FIG. 4, spine 18a has been advanced longitudinally, causing it to bow outwards to a greater degree which brings it into closer conformance with the tissue being investigated. Likewise, the electrodes on spine 18a may be in closer proximity and/or more electrodes may be in contact with the tissue in order to more accurately measure electrical signals. Similarly, each spine 18 may be individually manipulated to more closely conform to the surrounding tissue.

When basket-shaped electrode assembly 16 has been positioned and the relative longitudinal position of one or more spines 18 has been adjusted as desired, the electrophysiologist may map local activation time and/or ablate using electrodes 20, which can guide the electrophysiologist in diagnosing and providing therapy to the patient. The catheter may include one or more reference ring electrodes mounted on the catheter body and/or one or more reference electrodes may be placed outside the body of the patient. By using the inventive catheter with the one or more electrodes on the basket-shaped electrode assembly 16 brought into closer proximity or contact with tissue by adjusting the longitudinal position of one or more spines 18, the electrophysiologist can obtain a true anatomy of a cavernous region of the heart, including an atrium, by measuring less points than with traditional catheters, allowing a more rapid mapping of the region.

Figure 5:
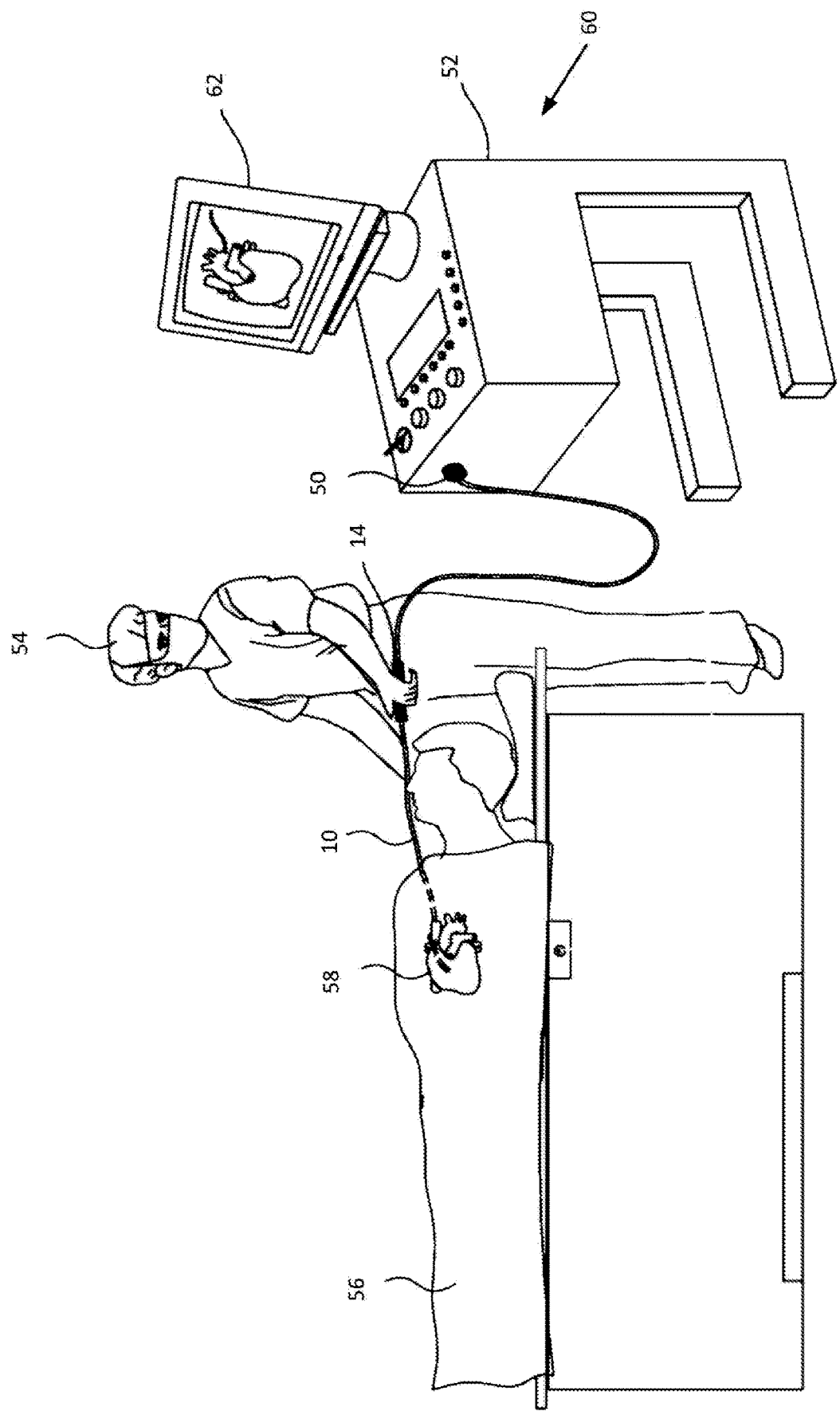
FIG. 5 is a schematic illustration of an invasive medical procedure using a basket-shaped electrode assembly with independently controlled spines, according to one embodiment.

To help illustrate use of basket-shaped electrode assembly 16 with individually controllable spines 18, FIG. 5 is a schematic depiction of an invasive medical procedure, according to an embodiment of the present invention. Catheter 10, with the basket-shaped electrode assembly 16 (not shown in this view) at the distal end may have a connector 50 for coupling the wires from actuators 22 and their associated electrodes 20 (not shown in this view) to a console 52 for recording and analyzing the signals they detect. An electrophysiologist 54 may insert the catheter 10 into a patient 56 in order to acquire electropotential signals from the heart 58 of the patient. The professional uses the control handle 14 attached to the catheter in order to perform the insertion. Console 52 may include a processing unit 60 which analyzes the received signals, and which may present results of the analysis on a display 62 attached to the console. The results are typically in the form of a map, numerical displays, and/or graphs derived from the signals.

In a further aspect, the processing unit 60 may also receive signals from one or more location sensors 30 provided near a distal end of the catheter 10 adjacent the basket-shaped electrode assembly 16 as schematically indicated in FIG. 1. The sensor(s) may each comprise a magnetic-field-responsive coil or a plurality of such coils. Using a plurality of coils enables six-dimensional position and orientation coordinates to be determined. The sensors may therefore generate electrical position signals in response to the magnetic fields from external coils, thereby enabling processor 60 to determine the position, (e.g., the location and orientation) of the distal end of catheter 10 within the heart cavity. The electrophysiologist may then view the position of the basket-shaped electrode assembly 16 on an image the patient's heart on the display 62. By way of example, this method of position sensing may be implemented using the CARTO™ system, produced by Biosense Webster Inc. (Diamond Bar, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference. As will be appreciated, other location sensing techniques may also be employed. If desired, at least two location sensors may be positioned proximally and distally of the basket-shaped electrode assembly 16. The coordinates of the distal sensor relative to the proximal sensor may be determined and, with other known information pertaining to the curvature of the spines 18 of the basket-shaped electrode assembly 16 as dependent on their relative longitudinal position, used to find the positions of each of the electrodes 20.

The preceding description has been presented with reference to presently disclosed embodiments of the invention. Workers skilled in the art and technology to which this invention pertains will appreciate that alterations and changes in the described structure may be practiced without meaningfully departing from the principal, spirit and scope of this invention. As understood by one of ordinary skill in the art, the drawings are not necessarily to scale. Accordingly, the foregoing description should not be read as pertaining only to the precise structures described and illustrated in the accompanying drawings, but rather should be read consistent with and as support to the following claims which are to have their fullest and fair scope.

What is claimed is:

1. A catheter comprising an elongated catheter body having proximal and distal ends and at least one lumen therethrough and a basket-shaped electrode assembly at the distal end of the catheter body, the basket-shaped electrode assembly comprising a plurality of spines connected at their distal ends, each spine comprising a flexible core wire with a nonconductive coating, the flexible core wire extending from the distal end to the proximal end of the catheter body, a plurality of electrodes, and cabling with embedded coiled lead wires within the nonconductive coating for connecting the electrodes and wherein the spines and the cabling with the embedded coiled lead wires extend through the lumen of the catheter body to the proximal end of the catheter body, each spine further comprising an actuator connected at a proximal end of each spine, the movement of each spine being independent of each other spine, whereby longitudinal movement of each spine is independently controlled by its respective actuator; and wherein each respective actuator comprises a connector at the proximal end of the elongated catheter body, the connector configured to couple wires from each respective actuator and associated plurality of electrodes.

2. The catheter of claim 1, wherein each spine is independently controlled by adjusting a longitudinal position relative to the catheter body.

3. The catheter of claim 1, wherein the basket-shaped electrode assembly has an expanded configuration in which each of the spines bow radially outwardly with a length unconstrained by the catheter body and a collapsed configuration in which the spines are arranged generally along a longitudinal axis of the catheter body.

4. The catheter of claim 3, wherein each spine is in a retracted position within respect to the catheter body when in the collapsed configuration.

5. The catheter of claim 3, wherein each of the spines are configured to bow outwards to a greater degree when positioned relatively more distally to increase the unconstrained length when the basket-shaped electrode assembly is in the expanded configuration.

6. The catheter of claim 3, wherein each of the spines may bow outwards to a lesser degree when positioned relatively more proximally to decrease the unconstrained length when the basket-shaped electrode assembly is in the expanded configuration.

7. The catheter of claim 1, wherein each spine comprises a shape memory material.

8. A method for mapping a cavity of the body comprising:
providing an elongated catheter body having proximal and distal ends and at least one lumen therethrough and a basket-shaped electrode assembly at the distal end of the catheter body, the basket-shaped electrode assembly comprising a plurality of spines connected at their distal ends, each spine comprising a flexible core wire with a nonconductive coating, the flexible core wire extending from the distal end to the proximal end of the catheter body, a plurality of electrodes, and cabling with embedded coiled lead wires within the nonconductive coating for connecting the electrodes and wherein the spines and the cabling with the embedded coiled lead wires extend through the lumen of the catheter body to the proximal end of the catheter body, each spine further comprising an actuator connected at a proximal end of each spine; and wherein each respective actuator comprises a connector at the proximal end of the elongated catheter body, the connector configured to couple wires from each respective actuator and associated plurality of electrodes;
introducing the distal end of the catheter into the cavity;
expanding the basket-shaped electrode assembly from a collapsed configuration wherein the spines are arranged generally along a longitudinal axis of the catheter body to an expanded configuration, wherein each of the spines has a length unconstrained by the catheter body;
independently controlling at least one of the spines to increase contact between at least a portion of the electrodes of the spine with tissue forming the cavity, the movement of each spine being independent of each other spine; and
recording electrical data received from the at least a portion of the electrodes in contact with the tissue.

9. The method of claim 8, wherein independently controlling at least one of the spines comprises adjusting a longitudinal position of the at least one spine relative to the catheter body.

10. The method of claim 8, wherein the spines bow radially outwardly when in the expanded configuration.

11. The method of claim 10, wherein independently controlling at least one of the spines comprises positioning the at least one spine relatively more distally to increase the unconstrained length and cause the at least one spine to bow outwards to a greater degree.

12. The method of claim 10 wherein independently controlling at least one of the spines comprises positioning the at least one spine relatively more proximally to decrease the unconstrained length and cause the at least one spine to bow outwards to a lesser degree.

13. The method of claim 8, wherein the cavity of the body is an atrium of the heart.

14. The method of claim 8, further comprising independently controlling a plurality of the spines.

* * * * *